(12) United States Patent
Petersen et al.

(10) Patent No.: US 6,426,422 B1
(45) Date of Patent: Jul. 30, 2002

(54) METHOD FOR THE PREPARATION OF CITALOPRAM

(75) Inventors: Hans Petersen, Vanløse; Haleh Ahmadian, Solrød Strand, both of (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/930,107

(22) Filed: Aug. 14, 2001

(30) Foreign Application Priority Data

Aug. 18, 2000 (DK) ........................................ 2000 01231

(51) Int. Cl.[7] ................... C07D 307/78; C07D 307/87; C07F 7/10; C07F 7/04
(52) U.S. Cl. ........................................ 549/467; 558/423
(58) Field of Search ........................... 549/467; 558/423

(56) References Cited

U.S. PATENT DOCUMENTS

| | | | |
|---|---|---|---|
| 3,467,675 A | | 9/1969 | Petersen et al. ......... 260/346.2 |
| 4,136,193 A | * | 1/1979 | Bogeseo et al. ............ 549/467 |
| 4,650,884 A | * | 3/1987 | Bogeseo et al. ............ 549/467 |
| 4,943,590 A | | 7/1990 | Boegesoe et al. ........... 415/469 |
| 5,296,507 A | | 3/1994 | Tanaka et al. .............. 514/465 |
| 6,020,501 A | | 2/2000 | Massonne et al. .......... 549/307 |
| 6,028,204 A | | 2/2000 | Massonne et al. .......... 549/307 |
| 6,229,026 B1 | | 5/2001 | Petersen ...................... 549/467 |
| 6,258,842 B1 | | 7/2001 | Petersen et al. ............. 514/469 |
| 6,291,689 B1 | * | 9/2001 | Petersen et al. ............. 549/467 |

FOREIGN PATENT DOCUMENTS

| | | | |
|---|---|---|---|
| EP | 0 171 943 | 2/1986 | ......... C07C/121/80 |
| EP | 0 474 580 | 3/1992 | ........... A61K/31/34 |
| EP | 1 095 926 | 5/2001 | ........... C07C/33/46 |
| WO | 98/19511 | 5/1998 | |
| WO | 98/19512 | 5/1998 | |
| WO | 98/19513 | 5/1998 | |
| WO | 98/28293 | 7/1998 | ......... C07D/401/04 |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |
| WO | 01/47877 | 7/2001 | |
| WO | WO 01/66536 | * 9/2001 | .................. 549/467 |

OTHER PUBLICATIONS

U.S. Patent Application Serial No. 09/794,762, filed Feb. 26, 2001.
U.S. Patent Application Serial No. 09/794,755, filed Feb. 26, 2001.
U.S. Patent Application Serial No. 09/830,109, filed Oct. 19, 1999 (International filing date).
U.S. Patent Application Serial No. 09/888,067, filed Jun. 22, 2001.
U.S. Patent Application Serial No. 09/891,874, filed Jun. 25, 2001.
U.S. Patent Application Serial No. 09/917,180, filed Jul. 27, 2001.
U.S. Patent Application Serial No. 09/692,653, filed Oct. 19, 2000.
U.S. Patent Application Serial No. 09/930,110, filed Aug. 14, 2001.
U.S. Patent Application Serial No. 09/977,920, filed Oct. 15, 2001.
U.S. Patent Application Serial No. 10/012,054, filed Nov. 6, 2001.
U.S. Patent Application Serial No. 10/012,025, filed Nov. 6, 2001.
U.S. Patent Application Serial No. 10/035,005, filed Dec. 20, 2001.
Levy, L.F., "4–Aminophthalide and Some Derivatives", *J. Chem. Soc.* pp. 867–870 (1931).
Tirouflet J., "Phtalide Substitutes en 5", *Bull. Soc. Sci. de Bretagne* 26:35–43 (1951).
Bigler, Allan et al., "Quantitative Structure–activity Relationships in a Series of Selective 5–HT uptake inhibitors," *Eur. J. Med. Chem.* 3:289–295 (1997).

* cited by examiner

*Primary Examiner*—Alan L. Rotman
*Assistant Examiner*—Raymond Covington
(74) *Attorney, Agent, or Firm*—Darby & Darby

(57) ABSTRACT

Disclosed is a method for the preparation of citalopram comprising conversion of a compound of Formula VIII

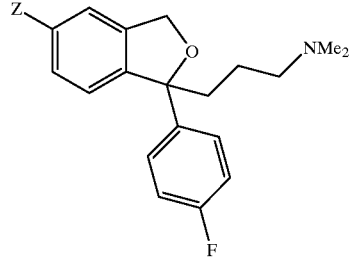

Formula VIII wherein Z is halogen, to a compound of Formula IV

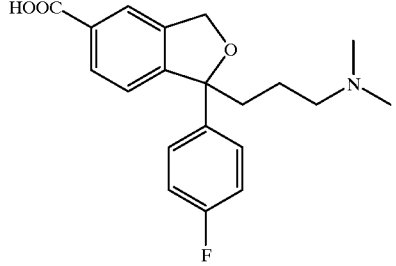

Formula IV followed by conversion of the compound of Formula IV into citalopram. Methods for the preparation of the compound of Formula IV are also disclosed.

14 Claims, No Drawings

METHOD FOR THE PREPARATION OF CITALOPRAM

The present invention relates to a method for the preparation of the well-known anti-depressant drug citalopram, 1-[3-(dimethylamino)propyl]-1-(4-fluorophenyl)-1,3-dihydro-5-isobenzofurancarbonitrile, methods for the preparation of intermediates used in the preparation of citalopram, and methods for conversion of said intermediates into citalopram.

BACKGROUND OF THE INVENTION

Citalopram is a well-known antidepressant drug that has now been on the market for some years and has the following structure:

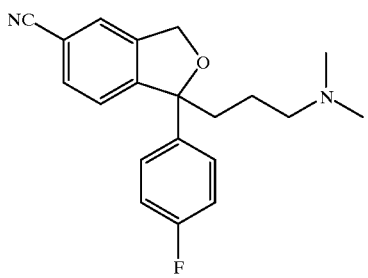

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A 474580.

Citalopram was first disclosed in DE 2,657,013, corresponding to U.S. Pat. No. 4,136,193. This patent publication describes the preparation of citalopram by one method and outlines a further method, which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

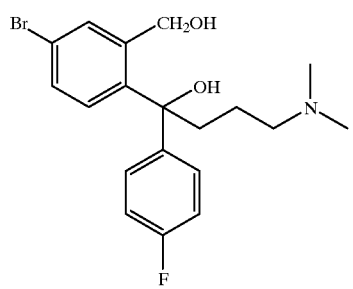

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884, according to which an intermediate of Formula III

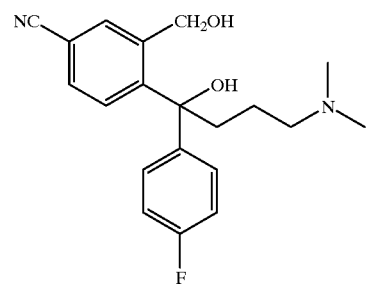

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively.

Further processes are disclosed in international patent application Nos. WO 98019511, WO 98019512 and WO 98019513. WO 98019512 and WO 98019513 relate to methods wherein a 5-amino-, 5-alkoxycarbonyl- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98019511 discloses a process for the manufacture of citalopram wherein a (4-substituted-2-hydroxymethylphenyl-(4-fluorophenyl)methanol compound is subjected to ring closure and the resulting 5-substituted 1-(4-fluorophenyl)-1,3-dihydroisobenzofuran converted to the corresponding 5-cyano derivative, which is alkylated with a (3-dimethylamino)propylhalogenide in order to obtain citalopram.

Finally, methods of preparing the individual enantiomers of citalopram are disclosed in U.S. Pat. No. 4,943,590 from which it also appears that the ring closure of the intermediate of Formula III may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram having the Formula I

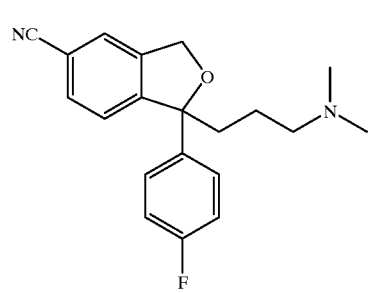

Formula I comprising:
conversion of a compound of Formula VIII

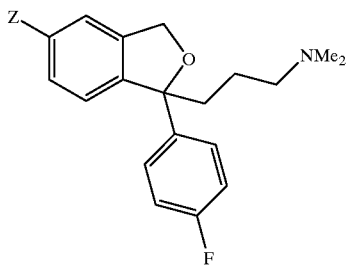

Formula VIII wherein Z is halogen,
to a compound of Formula IV

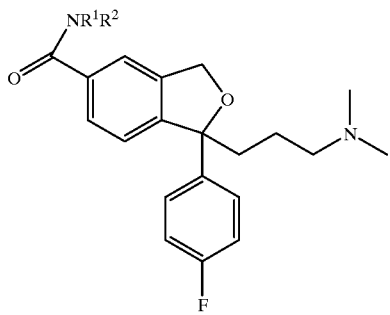

Formula IV followed by conversion of the compound of Formula IV into citalopram.

In particular the invention relates to such a method comprising:
i) reaction of the compound of Formula IV with a dehydrating agent and a sulfonamide of the Formula H$_2$N—SO$_2$—R wherein R is:
   a) An optionally substituted NH$_2$, or C$_{1-6}$ alkyloxy,
   b) aryloxy or heteroaryloxy optionally substituted with halogen, C$_{1-4}$-alkyl, cyano, hydroxy, C$_{1-4}$-alkoxy, trifluoromethyl, nitro, amino, C$_{1-4}$-alkylamino or di-C$_{1-4}$-alkylamino, or
   c) aryl or heteroaryl optionally substituted with halogen, C$_{1-4}$-alkyl, cyano, hydroxy, C$_{1-4}$-alkoxy, trifluoromethyl, nitro, amino, C$_{1-4}$-alkylamino or di-C$_{1-4}$-alkylamino; or
ii) conversion of the compound of Formula IV to the corresponding amide of Formula V

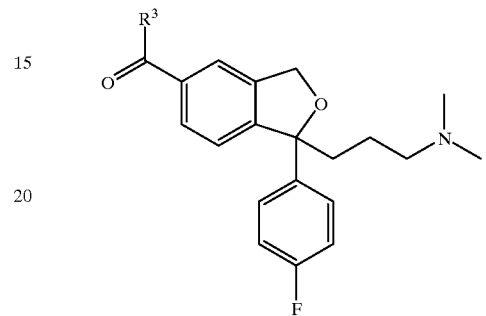

Formula V in which R$^1$ and R$^2$ are independently hydrogen, C$_{1-6}$ alkyl, C$_{1-6}$ alkyl substituted with one or more substituents selected from the group comprising aryl and heteroaryl, hydroxy, C$_{1-6}$-alkoxy, aryloxy, heteroaryloxy, aryl-C$_{1-6}$-alkoxy, or trisubstituted silyl wherein the substituents are independently C$_{1-6}$ alkyl, aryl, heteroaryl or aryl-C$_{1-6}$-alkyl and then reacting the amide of Formula V with a dehydrating agent
thereby obtaining citalopram as the base or a pharmaceutically acceptable salt thereof.

The conversion of the 5-carboxy derivative of Formula IV to the amide of Formula V may be carried out via activated acid derivative of Formula VI:

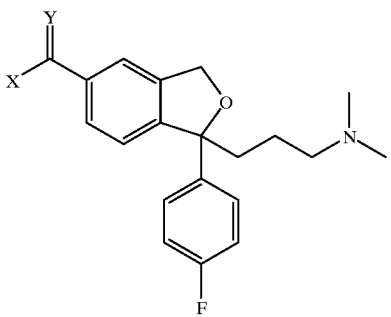

Formula VI wherein R$^3$ is halogen, C$_{1-6}$ alkoxy, aryloxy, heteroaryloxy, aryl-C$_{1-6}$-alkoxy, heteroaryl-C$_{1-6}$-alkoxy, alkylcarbonate, arylcarbonate, alkylcarbamate, arylcarbamate, alkylthiocarbonate, arylthiocarbonate, alkylthiocarbamate, arylthiocarbamate, alkylacyloxy, arylacyloxy, substituted or unsubstituted aryl or substituted or unsubstituted heteroaryl.

In another aspect, the invention relates to methods for the preparation of the intermediate of Formula IV comprising conversion of a compound of Formula VIII, wherein Z is halogen to compound of Formula IV.

In yet another aspect, the invention relates to methods for the preparation of the intermediate of Formula VII Formula VII wherein X is selected from halide, CN, OR$^5$ or SR$^6$ where R$^5$ and R$^6$ are independently selected from C$_{1-6}$ alkyl, aryl, heteroaryl or benzyl and each of these C$_{1-6}$ alkyl, aryl, heteroaryl or benzyl groups are unsubstituted or substituted with halogen, C$_{1-4}$ alkyl, cyano, hydroxy, C$_{1-4}$ alkoxy, trifluoromethyl, nitro, amino, C$_{1-4}$ alkylamino or di-C$_{1-4}$ alkylamino, NR$^7$R$^8$ where R$^7$ and R$^8$ are independently selected from hydrogen, C$_{1-6}$ alkyl, aryl, heteroaryl or benzyl and each of these C$_{1-6}$ alkyl, aryl, heteroaryl or benzyl groups are unsubstituted or substituted with halogen, C$_{1-4}$ alkyl, cyano, hydroxy, C$_{1-4}$ alkoxy, trifluoromethyl, nitro, amino, C$_{1-4}$ alkylamino or di-C$_{1-4}$ alkylamino;
Y is O, S, or NR$^9$ where R$^9$ is selected from hydrogen, C$_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$-alkylamino;

comprising conversion of a compound of Formula VIII

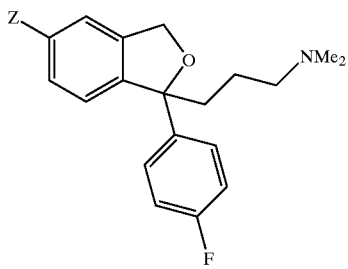

Formula VIII wherein Z is halogen, to a compound of Formula VII.

In yet another aspect, the present invention relates to an antidepressant pharmaceutical composition comprising citalopram as the base or any convenient salt thereof manufactured by the process of the invention.

Throughout the specification and claims, the term 'dehydrating agent' refers to any suitable dehydrating agent, and a person skilled in the art may easily determine the optimal agent. Examples of suitable dehydrating agents are $SOCl_2$, $POCl_3$, $PCl_5$, $SOBr_2$, $POBr_3$, $PBr_5$, $SOI_2$, $POI_3$, $PI_5$, $P_4O_{10}$, oxalylchloride, carbonyldiimidazole and Vilsmeier reagents. Preferably a chloro-containing agent, most preferably $SOCl_2$ or $POCl_3$, is used. Vilsmeier reagents are reagents formed by mixing of N,N-dimethylformamide (DMF) and dehydrating agents, examples of which are DMF/$SOCl_2$ and DMF/$POCl_3$.

Throughout the specification and claims, $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2,2-dimethyl-1-ethyl and 2-methyl-1-propyl. Similarly, $C_{1-4}$ alkyl refers to such a group having from one to four carbon atoms inclusive and $C_{1-6}$ alkoxy, $C_{1-4}$ alkoxy and $C_{1-4}$ alkylamine designate such groups wherein the alkyl moity is as defined.

Halogen means fluorine, chlorine, bromine or iodine.

In the method i) of the invention, one possible but non-limiting mechanism of the reaction is that the 5-carboxy compound of Formula IV reacts with the dehydration agent in order to form a corresponding activated derivative, which then reacts with the sulfonamide, $H_2N-SO_2-R$, thereby forming citalopram. During the latter reaction, a catalytic amount of an acid may be necessary.

The sulfonamide, $H_2N-SO_2-R$, used in the process is preferably sulfamide, $NH_2-SO_2-NH_2$.

The optionally substituted $NH_2$ used in the process is preferably tert-butylamine.

The reactions with dehydration agents in the method of the invention are carried out neat or in a suitable solvent, such as sulfolane or acetonitrile. When a solvent is used in the dehydration reaction of ii), a catalytic amount of N,N-dimethylformamide may be needed.

In preferred embodiments of the invention, the methods for preparation of citalopram and/or the compounds of Formula IV or Formula VII comprises:

a) Reaction of the 5-halo analogue of Formula VIII

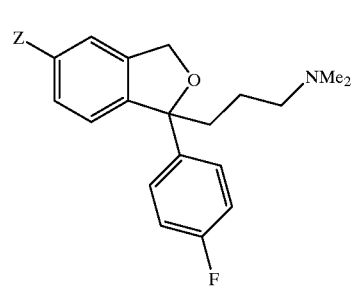

Formula VIII wherein Z is halogen, with Mg or an organolithium compound, e.g. n-BuLi, or with an organometallic complex composed of Mg and/or Mn and/or Li and alkyl or aryl groups and subsequently with $CO_2$, $CS_2$ or a compound of the Formula IX

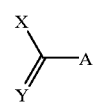

Formula IX wherein A and X are independently selected from halide, CN, $OR^5$ or $SR^6$ where $R^5$ and $R^6$ are independently selected from $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino, $NR^7R^8$ where $R^7$ and $R^8$ are independently selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino; Y is O, S, or $NR^9$ where $R^9$ is selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino;

and in the methods for manufacture of citalopram or compounds of Formula IV followed by reaction with water, a hydroxide such as NaOH, or an aqueous solution of an acid;

b) coupling of a compound of Formula VIII

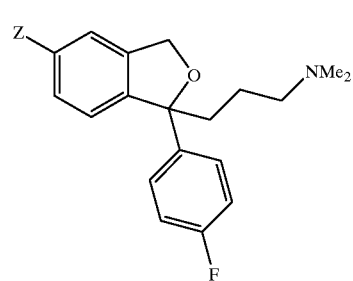

Formula VIII wherein Z is Br or I with an optionally substituted vinyl or acetylenic group in the presence of a metal catalyst, such as a nickel or palladium based catalyst, followed by oxidation of the vinyl or acetylenic group to carboxy thereby obtaining the compound of Formula IV.

In method a), examples of organometallic complexes are trialkylmagnesates of the Formula $(R^4)_3MgLi$, trialkylmanganates of the Formula $(R^4)_3MnLi$ and mixed magnesium and mangenate complexes of the Formula $(R^4)_3MnMgBr$, wherein $R^4$ designates $C_{1-6}$-alkyl or aryl groups that may be identical or different. Trialkylmagnesate may be prepared in situ from a Grignard reagent $R^4MgX$ (X is halogen) and an organolithium, e.g. n-butyllithium. Trialkylmangenate may be generated in situ from $MnCl_2$ and an organolithium e.g. n-butyllithium. $(R^4)_3MnMgBr$ may be prepared from a Grignard reagent $R^4MgX$ and $MnCl_2$. The starting 5-bromo compound of Formula VIII may be obtained as described in U.S. Pat. No. 4,136,193.

In method a), examples of starting materials of Formula IX are: ethyl chloroformate, phenyl chloroformate, benzyl chloroformate, vinyl chloroformate, isobutyl chloroformate, ethyl chlorothiolformate, methyl cyanoformate, carbonyldi-imidazole and diethyl carbonate. The starting materials of Formula IX are commercially available or may be prepared by literature methods.

In method b), the nickel based catalyst may be any suitable Ni(0) or Ni(II) containing complex which acts as a catalyst, such as $Ni(PPh_3)_3$ and $(\sigma\text{-aryl})\text{-}Ni(PPh_3)_2Cl$, and the palladium based catalyst may be any suitable Pd(0) or Pd(II) containing catalyst, such as $Pd(PPh_3)_4$, $Pd_2(dba)_3$ and $Pd(PPh)_2Cl_2$. The oxidation agent may be any suitable agent, such as a peroxide in the presence of a ruthenium catalyst. The starting compounds wherein B is a triflate group may be obtained as described in WO 0013648. Examples of the vinyl or acetylenic groups coupled with the compound of Formula VIII are methyl acrylate, 1-bromobut-1-ene, propyne, trimethyl(prop-1-enyl) stannane, E-1-hexenylboronic acid and prop-1-enyl trifluoromethylsulfonate.

The compound of Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as diethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical Formulations of the invention may be prepared by conventional methods in the art. For example, tablets may be prepared by mixing the active ingredient with ordinary adjuvants and/or diluents and subsequently compressing the mixture in a conventional tabletting maschine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

EXAMPLES

The invention is further illustrated by the following examples, which should not be construed as limiting the scope of the invention.

Example 1

5-Carboxy-1-(4-fluorophenyl)-1-(3-dimethylaminopropyl)-1,3-dihydro-isobenzofuran Method a)—Mg A solution of 1-(4-fluorophenyl)-1-(3-dimethylaminopropyl)-1,3-dihydro-isobenzofuran-5-yl magnesium bromide in dry THF (90 mL) (prepared by ordinary methods from 5-bromo-1-(4-fluorophenyl)-1-(3-dimethylaminopropyl)-1,3-dihydro-isobenzofuran (9 g, 0.024 mole) and magnesium (0.73 g, 0.03 mole)) was added to dry solid $CO_2$ (50 g). After addition, the mixture was left at room temperature for 16 hours. The volatile materials were removed in vacuo and the residue was taken up in water (100 mL). pH was adjusted to 5.5 by adding HCl (aqueous, 4 N). The aqueous phase was extracted with toluene (100 mL). The toluene was removed in vacuo and the title compound was obtained as oil. Yield 6 grams.

Method a)—n-BuLi

To a solution of 5-bromo-1-(4-fluorophenyl)-1-(3-dimethylaminopropyl)-1,3-dihydro-isobenzofuran (9 g, 0.024 mole) in tert.butyl methyl ether (150 mL) was added n-BuLi (1.6 M in hexanes, 40 mL) at −78° C. to −65° C. The temperature of the solution was allowed to raise to −30° C. over a period of 2 hours. The reaction mixture was added to dry solid $CO_2$ (50 g). After addition, the mixture was left at room temperature for 16 hours. The volatile materials were removed in vacuo and the residue was taken up in water (100 mL). pH was adjusted to 5.5 by adding HCl (aqueous, 4 N). The aqueous phase was extracted with toluene (100 mL). The toluene was removed in vacuo and the title compound was obtained as an oil. Yield 7.5 grams.

Method a)—trialkylmagnesate n-BuLi (20 mL, 1.6 M in hexane) was added to a solution of isopropylmagnesium chloride (8.0 mL, 2 M in diethylether) in THF (25 mL) at 0° C. The resulting mixture was stirred at 0° C. for 1 h, then cooled to −78° C. and a solution of 5-bromo-1-(4-fluorophenyl)-1-(3-dimethylaminopropyl)-1,3-dihydro-isobenzofuran (5.0 g, 13.0 mmol) in THF (25 mL) was added. The mixture was allowed to warm to −10° C. during 1 h, then cooled again to −78° C. and $CO_2$ (5.7 g, 130 mmol) was added. The mixture was allowed to warm to room temperature, and then evaporated. Ion exchange chromatography of the residue (Dowex®-50, acidic form) eluting with 1 M $NH_3$ afforded the product as a thick oil.

Example 2

5-Cyano-1-(4-fluorophenyl)-1-(3-dimethylaminopropyl)-1,3-dihydro-isobenzofuran (Citalopram, free base)

5-Carboxy-1-(4-fluorophenyl)-1-(3-dimethylaminopropyl)-1,3-dihydro-isobenzofuran (5 g, 0.015 mole) and sulfamide (1.65 g, 0.017 mole) were dissolved in sulfolane (15 mL). Thionylchloride (2.25 g, 0.019 mole) was added at room temperature and the temperature of the reaction mixture was raised to 130° C. for 2 hours. The reaction mixture was allowed to cool to 75° C. and water (25 mL) was added. The temperature was held at 75° C. for 15 min, and then the reaction mixture was cooled to room temperature. pH was ajusted to 9 with ammonium hydroxide and then n-heptane (75 mL) was added. The temperature was raised to 70° C. and the hot n-heptane layer was isolated from which the title compound crystallised on cooling. Yield 3.77 g. Purity (HPLC peak area)>97%.

What is claimed is:

1. A method for the preparation of citalopram

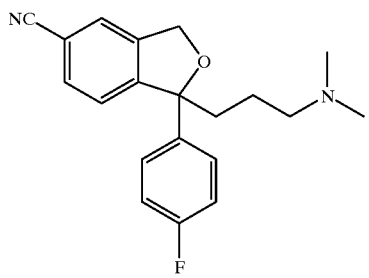

Formula I comprising
conversion of a compound of Formula VIII

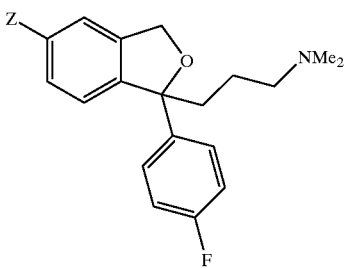

Formula VIII wherein Z is halogen,
to a compound of Formula IV

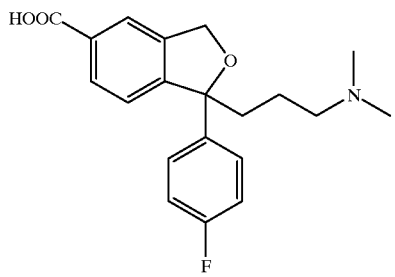

Formula IV followed by conversion of the compound of Formula IV into citalopram.

2. A method according to claim 1, wherein:
   i) the compound of Formula IV is reacted with a dehydrating agent and a sulfonamide of the Formula $H_2N$—$SO_2$—R wherein R is:
      a) an optionally substituted $NH_2$, or $C_{1-6}$ alkyloxy,
      b) aryloxy or heteroaryloxy optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino, or
      c) aryl or heteroaryl optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino; or
   ii) the compound of Formula IV is converted to the corresponding amide of Formula V

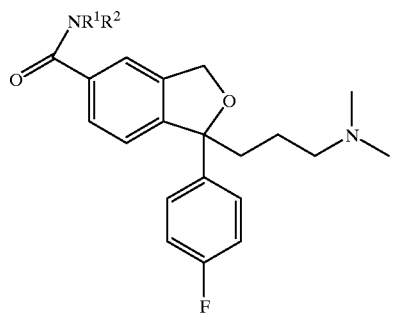

Formula V in which $R^1$ and $R^2$ are independently hydrogen, $C_{1-6}$ alkyl, $C_{1-6}$ alkyl substituted with one or more substituents selected from the group consisting of aryl and heteroaryl, hydroxy, $C_{1-6}$-alkoxy, aryloxy, aryl-$C_{1-6}$-alkoxy, or trisubstituted silyl wherein the substituents are independently $C_{1-6}$ alkyl, aryl, heteroaryl or aryl-$C_{1-6}$-alkyl and then reacting the amide of Formula V with a dehydrating agent thereby obtaining citalopram as the base or a pharmaceutically acceptable salt thereof.

3. The method according to claim 2, wherein the compound of Formula IV is reacted with $SOCl_2$ and sulfamide.

4. The method of claim 3, wherein the reaction is performed in sulfolan.

5. The method of claim 2, wherein the compound of Formula IV is reacted with $POCl_3$ and tert-butylamine.

6. The method of claim 1, wherein the compound of Formula IV is obtained by:
   i) reacting the compound of Formula VIII

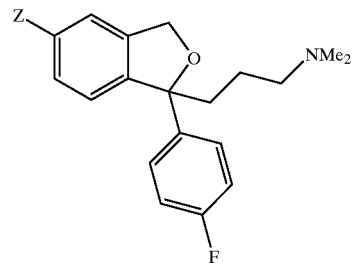

Formula VIII wherein Z is halogen, with Mg or an organolithium compound, or with an organometallic complex composed of Mg and/or Mn and/or Li and alkyl or aryl groups to achieve a first intermediate;

ii) subsequently reacting said first intermediate with CO$_2$, CS$_2$ or a compound of Formula IX

Formula IX wherein A and X are independently selected from halide, CN, OR$^5$ or SR$^6$ where R$^5$ and R$^6$ are independently selected from C$_{1-6}$ alkyl, aryl, heteroaryl or benzyl and each of these C$_{1-6}$ alkyl, aryl, heteroaryl or benzyl groups are unsubstituted or substituted with halogen, C$_{1-4}$ alkyl, cyano, hydroxy, C$_{1-4}$ alkoxy, trifluoromethyl, nitro, amino, C$_{1-4}$ alkylamino or di-C$_{1-4}$ alkylamino, NR$^7$R$^8$ where R$^7$ and R$^8$ are independently selected from hydrogen, C$_{1-6}$ alkyl, aryl, heteroaryl or benzyl and each of these C$_{1-6}$ alkyl, aryl, heteroaryl or benzyl groups are unsubstituted or substituted with halogen, C$_{1-4}$ alkyl, cyano, hydroxy, C$_{1-4}$ alkoxy, trifluoromethyl, nitro, amino, C$_{1-4}$ alkylamino or di-C$_{1-4}$ alkylamino; Y is O, S, or NR$^9$ where R$^9$ is selected from hydrogen, C$_{1-6}$ alkyl, aryl, heteroaryl or benzyl and each of these C$_{1-6}$ alkyl, aryl, heteroaryl or benzyl groups are unsubstituted or substituted with halogen, C$_{1-4}$ alkyl, cyano, hydroxy, C$_{1-4}$ alkoxy, trifluoromethyl, nitro, amino, C$_{1-4}$ alkylamino or di-C$_{1-4}$ alkylamino;

to achieve a second intermediate;

iii) and subsequently reacting said second intermediate with water, a hydroxide such as NaOH, or an aqueous solution of an acid.

7. The method of claim 1, wherein the compound of Formula IV is obtained by coupling of a compound of Formula VIII

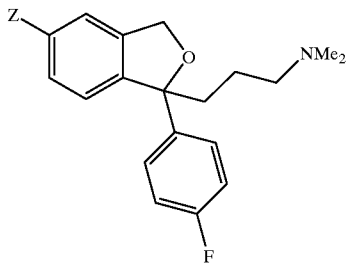

Formula VIII wherein Z is Br or I with an optionally substituted vinyl or acetylenic group in the presence of a metal catalyst, followed by oxidation of the vinyl or acetylenic group to carboxy thereby obtaining the compound of Formula IV.

8. A method for the preparation of a compound of Formula IV

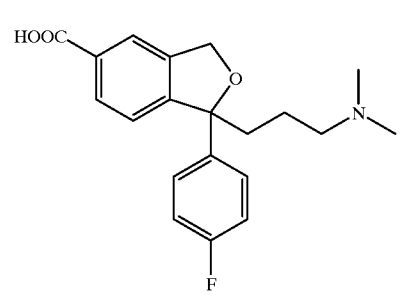

Formula IV comprising conversion of a compound of Formula VIII

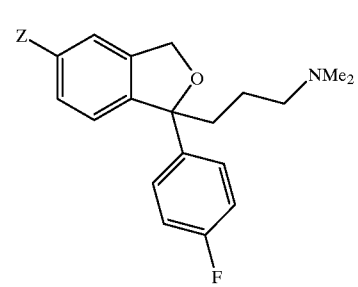

Formula VIII wherein Z is halogen, to a compound of Formula IV.

9. The method of claim 8, wherein the compound of Formula IV is obtained by:

i) reacting the compound of Formula VIII

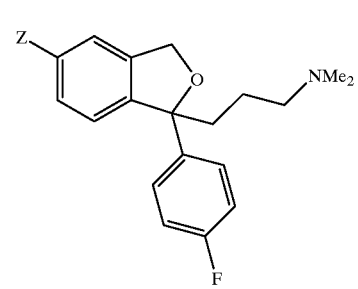

Formula VIII wherein Z is halogen, with Mg or an organolithium compound, or with an organometallic complex composed of Mg and/or Mn and/or Li and alkyl or aryl groups to achieve a first intermediate;

ii) subsequently reacting said first intermediate with CO$_2$, CS$_2$ or a compound of Formula IX

Formula IX wherein A and X are independently selected from halide, CN, OR$^5$ or SR$^6$ where R$^5$ and R$^6$ are independently selected from C$_{1-6}$ alkyl, aryl, heteroaryl or benzyl and each of these C$_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino, $NR^7R^8$ where $R^7$ and $R^8$ are independently selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino; Y is O, S, or $NR^9$ where $R^9$ is selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino;

to achieve a second intermediate;

iii) and subsequently reacting said second intermediate with water, a hydroxide such as NaOH, or an aqueous solution of an acid.

10. The method of claim 8, wherein the compound of Formula IV is obtained by coupling of a compound of Formula VIII

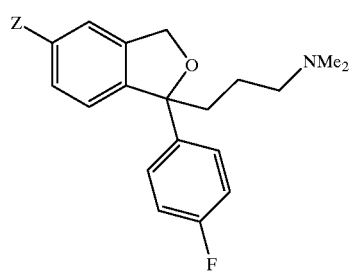

Formula VIII wherein Z is Br or I with an optionally substituted vinyl or acetylenic group in the presence of a metal catalyst, followed by oxidation of the vinyl or acetylenic group to carboxy thereby obtaining the compound of Formula IV.

11. A method for the preparation of a compound of Formula VII

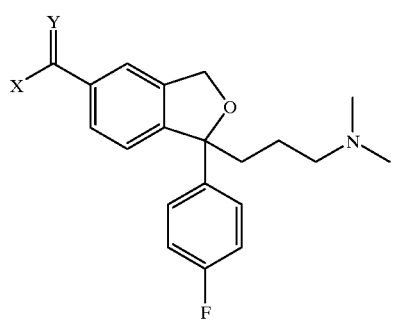

Formula VII wherein

X is selected from halide, CN, $OR^5$ or $SR^6$ where $R^5$ and $R^6$ are independently selected from $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino, $NR^7R^8$ where $R^7$ and $R^8$ are independently selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino;

Y is O, S, or $NR^9$ where $R^9$ is selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$-alkylamino;

comprising conversion of a compound of Formula VIII

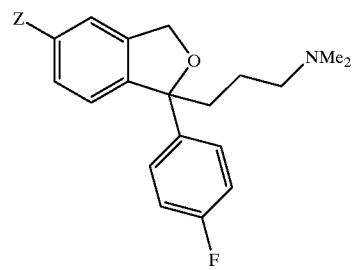

Formula VIII wherein Z is halogen, to a compound of Formula VII.

12. The method of claim 11, wherein the compound of Formula VII is obtained by:

i) reacting the compound of Formula VIII

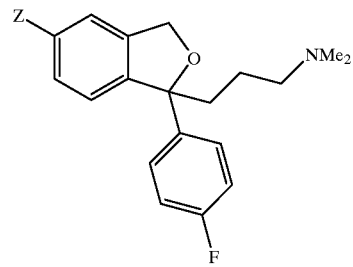

Formula VIII wherein Z is halogen, with Mg or an organolithium compound, or with an organometallic complex composed of Mg and/or Mn and/or Li and alkyl or aryl groups to achieve a first intermediate;

ii) subsequently reacting said first intermediate with $CO_2$, $CS_2$ or a compound of Formula IX

Formula IX wherein

A and X are independently selected from halide, CN, $OR^5$ or $SR^6$ where $R^5$ and $R^6$ are independently selected from $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino, $NR^7R^8$ where $R^7$ and $R^8$ are independently selected from hydrogen, $C_{1-6}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino;

Y is O, S, or $NR^9$ where $R^9$ is selected from hydrogen, $C_{1-4}$ alkyl, aryl, heteroaryl or benzyl and each of these $C_{1-6}$ alkyl, aryl, heteroaryl or benzyl groups are unsubstituted or substituted with halogen, $C_{1-4}$ alkyl, cyano, hydroxy, $C_{1-4}$ alkoxy, trifluoromethyl, nitro, amino, $C_{1-4}$ alkylamino or di-$C_{1-4}$ alkylamino;

to achieve the compound of Formula VII.

13. Citalopram as the base or any convenient salt thereof manufactured by the methods of claims 1 and 8.

14. A pharmaceutical composition comprising citalopram as the base or any convenient salt thereof according to claim 13.

* * * * *